United States Patent [19]
Sullivan

[11] 4,440,378
[45] Apr. 3, 1984

[54] FLOW CONTROL APPARATUS

[76] Inventor: Michael P. Sullivan, P.O. Box 175, Wasco, Oreg. 97065

[21] Appl. No.: 312,856

[22] Filed: Oct. 16, 1981

[51] Int. Cl.³ .............. F16K 7/02; F16K 51/00; A61M 5/00
[52] U.S. Cl. .............................. 251/117; 251/4; 604/249; 604/250
[58] Field of Search .......... 604/33, 34, 30, 249, 604/250; 251/117, 4

[56] References Cited

U.S. PATENT DOCUMENTS

| | | | |
|---|---|---|---|
| 1,983,227 | 12/1934 | Hall et al. | 158/115 |
| 2,181,900 | 12/1939 | Langdon | 137/93 |
| 2,229,903 | 1/1941 | Schmohl et al. | 277/57 |
| 2,706,101 | 4/1955 | Cantor | 251/4 |
| 3,107,894 | 11/1963 | Quinn | 251/118 |
| 3,298,367 | 1/1967 | Bergman | 128/214 |
| 3,675,891 | 7/1972 | Reynolds et al. | 251/117 |
| 3,840,207 | 10/1974 | Carpenter | 251/5 |
| 4,182,357 | 1/1980 | Ornstein | 251/4 X |
| 4,192,303 | 3/1980 | Young et al. | 128/214 |
| 4,210,178 | 7/1980 | Morse et al. | 604/249 X |

FOREIGN PATENT DOCUMENTS 355675 6/1922 Fed. Rep. of Germany .......... 251/4

*Primary Examiner*—Arnold Rosenthal
*Attorney, Agent, or Firm*—Lyon & Lyon

[57] ABSTRACT

A device including a valving mechanism which can be operated by one hand. The device includes a housing which surrounds a resilient block of material. The housing may be squeezed to depress and deform the resilient block. Passageways extend through the resilient block to conduct liquid therethrough. A first passage includes a solid valve positioned therein. Compression of the resilient block breaks the seal around the valve by distorting the passageway to allow flow therethrough. A second passage includes a capillary to allow continuous low volume flow not controlled by an operator.

12 Claims, 5 Drawing Figures

U.S. Patent  Apr. 3, 1984  4,440,378
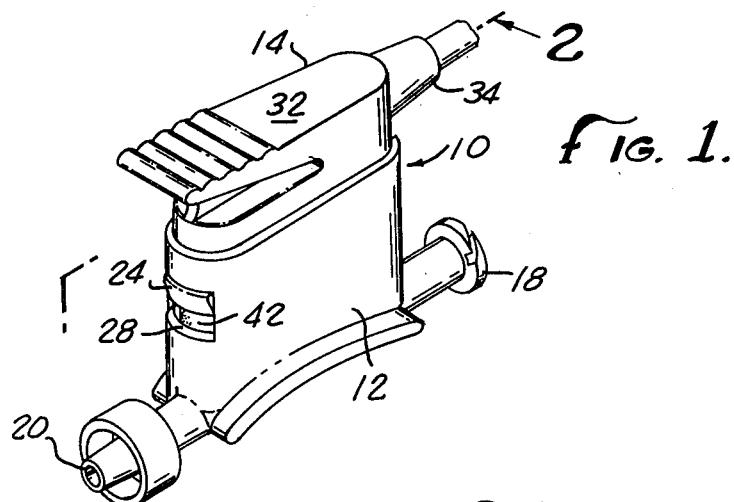
FIG. 1.
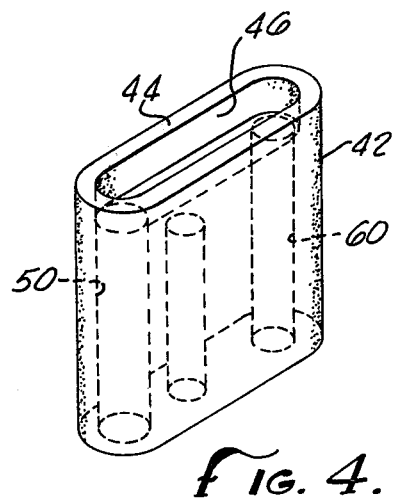
FIG. 4.
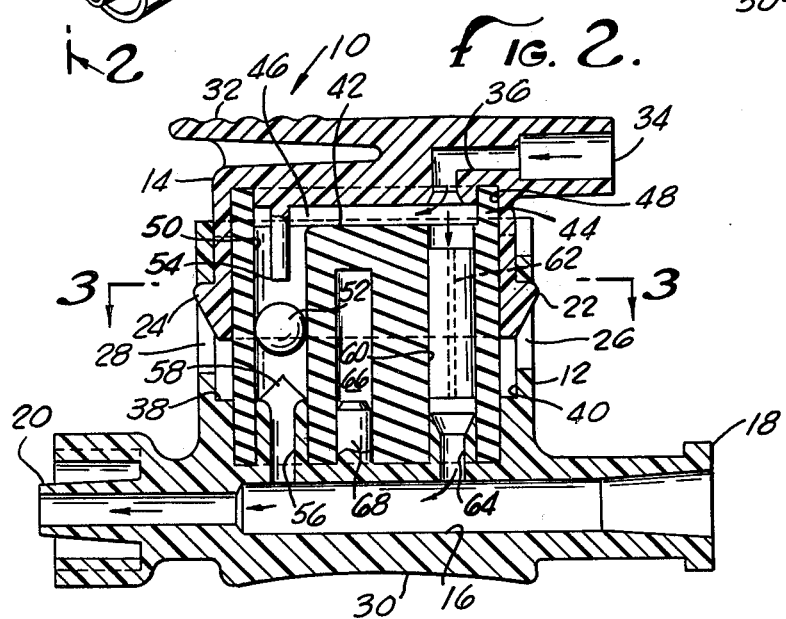
FIG. 2.
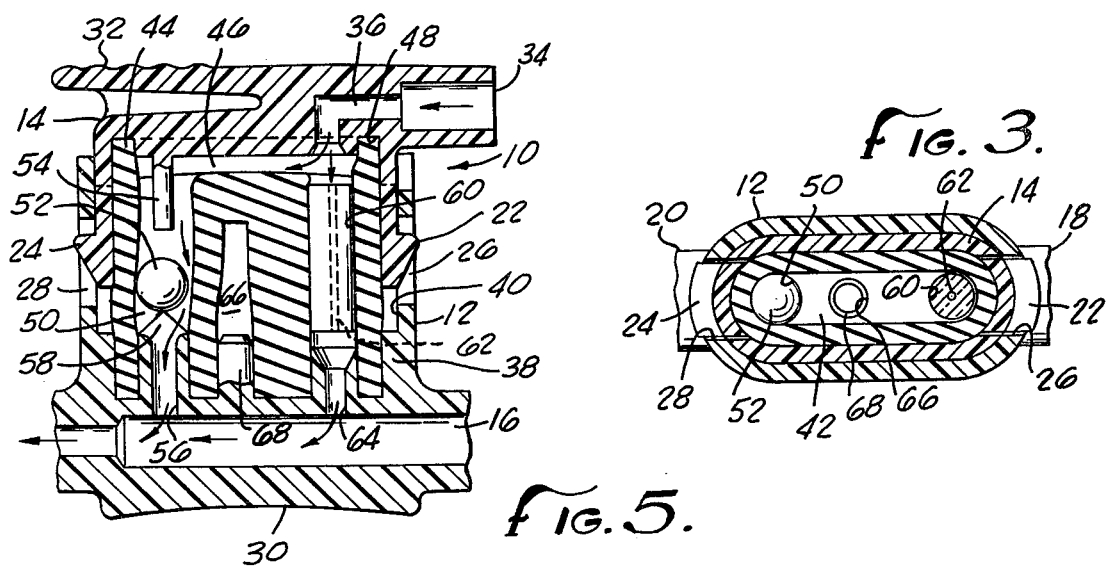
FIG. 3.
FIG. 5.

FLOW CONTROL APPARATUS

BACKGROUND OF THE INVENTION

The field of the present invention is flow control devices and particularly such devices as are employed with intravenous catheters.

With the advent of sophisticated monitoring equipment, it has become common practice in hospitals and particularly in intensive care facilities to maintain a continuous monitoring of certain body functions. This monitoring often includes intravenous sensing requiring a hollow catheter.

The advantages of continuous monitoring of blood pressure and the like using such a hollow catheter have made this practice routine. However, such catheters are subject to blinding by blood clotting over the end in the vein or artery. A relatively successful solution to such blinding has been devised which includes a small medical fluid flow through the catheter. To this end, capillary tubes have been employed. The capillary flow is, however, only a partial solution to the problem. Use of such a system requires a compromise between excessive volumes of flow into the body and insufficient flow to assure against blinding.

To prevent excessive flow into the body and yet provide some means for overcoming clotting, an additional solution has been employed. A manually controlled high volume flow sufficient to insure against blinding of the catheter is used. The high volume flow is also useful for initially filling the catheter line with fluid, for removing air bubbles and the like. Disclosures of such devices incorporating this bi-flow concept include U.S. Pat. No. 3,675,891 entitled "Continuous Catheter Flushing Apparatus" to Reynolds et al. and U.S. Pat. No. 4,192,303 entitled "Flow Restricting Device For Artificial Catheter Systems" to Young et al. The Reynolds et al. and Young et al. patents are incorporated herein by reference as indicative of the prior state of the art and to provide further illustration of utility of the present invention.

A difficulty remaining with the state of the art devices presently employed in hospitals and the like is that they are susceptible to being very inconvenient to use one-handed. Often the operator must be holding another container or in some other way using one hand for other purposes. Consequently, one-handed operation is quite important. Another difficulty is the susceptibility of the rather delicate components of such units to breakage. Heretofore, the valves have been either tricky to manipulate or so fragile as to require careful attention to prevent damage or inoperability.

SUMMARY OF THE INVENTION

The present invention is directed to a flow control device specifically designed for providing one-handed control. By manual control, the operator is able to operate a valving mechanism to effect what is considered high volume flow in such catheter systems. To accomplish the present invention a resilient block of material is employed with a passage therethrough. Positioned within the passage is a valve which is capable of closing the passage when the block of material is in a relaxed state. When the block is deformed, the fluid in the passageway is able to move around the valve to provide the requisite flow. When relaxed again, the block returns to its original shape and the valve is able to close the passage.

A mechanism has been devised to predictably deform the block of resilient material. This mechanism includes a housing having a central cavity. The housing is formed in two pieces with one capable of moving relative to the other such that with one hand an operator can squeeze the housing to deform the resilient block.

In combination with the high flow valving mechanism, a capillary may be provided which is arranged in parallel with the high flow passage. The capillary is designed to act independently of the valving mechanism to allow continuous, low volume flow to the catheter.

Another feature which may be employed with the present invention is the provision for a space within the cavity of the housing. The space is arranged near the valving mechanism to promote deformation of the passage wall to insure predictable high volume flow. In the preferred embodiment, this space is provided within the block of material. It may also be defined between the block of resilient material and the wall of the housing.

Generally, the present invention combining a squeezable housing with a block of resilient material containing a valving mechanism provides single-handed operation, is not easily breakable, and does not require close tolerances. Consequently, the device is believed to be reliable in performing its intended function in the critical and often demanding environment of hospital and intensive care treatment facilities.

Accordingly, it is an object of the present invention to provide an improved flow control mechanism.

It is a further object of the present invention to provide a reliable flow control mechanism capable of being operated with one hand.

Other and further objects and advantages will appear hereinafter.

BRIEF DESCRIPTION OF THE DRAWINGS

FIG. 1 is a perspective view of an assembled device of the present invention.

FIG. 2 is a cross-sectional elevation taken along line 2—2 of FIG. 1.

FIG. 3 is a cross-sectional plan taken along line 3—3 of FIG. 2.

FIG. 4 is a perspective view of a resilient block according to the present invention.

FIG. 5 is a cross-sectional elevation as in FIG. 2 with the resilient block in a deformed condition.

DETAILED DESCRIPTION OF THE PREFERRED EMBODIMENT

Turning in detail to the drawings, a preferred embodiment is illustrated as including a housing of rigid plastic material. The housing, generally designated 10, includes a hollow body 12 and a plunger 14. The hollow body 12 includes an upstanding, generally ovular side wall as best seen in plan in FIG. 3. The hollow body 12 further includes integrally formed therewith a through passageway 16 having a first end 18 and second end 20 capable of accommodating conventional catheter tubing and fittings.

The plunger 14 also includes an ovular wall as can best be seen in FIG. 3. The wall of the plunger 14 is designed to fit in telescoping fashion within the ovular wall of the hollow body 12. Together, the interior of the hollow body 12 and the plunger 14 define an ovular cavity which can be varied in height by telescoping the plunger into and out of the hollow body 12. Naturally, other shapes may be defined by the housing 10 without departing from the present invention. Furthermore, the telescoping arrangement may be reversed in that the upper portion becomes the housing and the lower portion the plunger in telescoping arrangement.

To fix the two parts, the hollow body 12 and the plunger 14, together to both provide relative motion and prevent complete separation of the components, two tapered keepers 22 and 24 are integrally formed with the plunger 14. The keepers are tapered for easy snapping together of the hollow body 12 and the plunger 14 and yet retain the parts together by means of the upper flanges thereon. The keepers are positioned in slots 26 and 28 through the ovular wall of the hollow body 12. The slots 26 and 28 provide sufficient depth to accommodate squeezing of the housing in operation, as illustrated in FIG. 5. It can be noted from FIG. 3 that the sidewall of the plunger 14 is slit upwardly adjacent the keepers 22 and 24. These slits are designed to give sufficient resiliency to the keepers 22 and 24 relative to the body of the plunger so that the plunger may be easily telescoped into the hollow body 12 at the time of assembly.

The undersurface 30 of the hollow body 12 and the upper surface of the plunger 32 are designed to give convenient manual purchase and are also sized to provide an easy grip for an average hand. The surfaces 30 and 32 may be roughened or provided with grooves such as illustrated in FIG. 1 to aid the operator in gripping the apparatus.

Located in the plunger 14 is an inlet 34 designed to accommodate conventional tubing or fittings employed with such devices. The inlet 34 includes a passageway 36 directed to the cavity in part defined by the plunger 14. Thus, medical fluids and the like can be admitted through the inlet 34 into the interior or central cavity of the housing 10.

To further define the central cavity, the hollow body 12 includes an inward step or flange 38 having the same inside cross-sectional dimensions as the plunger 14. Thus, the cavity is defined both top and bottom with a common cross-section for careful location of the resilient block contained therein at these points. Yet, an annular space is allowed at 40 accommodating some deformation of the resilient block. This space 40 also accommodates movement of the plunger as can be seen by comparing FIGS. 2 and 5.

The resilient block of material 42 contained within the central cavity of the housing 10 is shown independently in FIG. 4, in a relaxed state in FIG. 2, and in a compressed state in FIG. 5. This resilient material as employed in the preferred embodiment is a clear silicone rubber having a Shore hardness of A25. A wide range of hardnesses may be employed with the block 42 and will affect the amount of force required to actuate the mechanism.

The block 42 is generally ovular in shape to fit closely within the interior of the plunger 14 and the inner flange 38. It includes an upstanding ovular flange 44 forming a continuous wall with the main block of material. This upstanding flange 44 defines a cavity 46 which serves as a manifold for directing medical fluid passing into the central cavity through the passageway 36. To accommodate this upstanding flange 44, the plunger 14 includes a groove 48 in the undersurface thereof. The groove 48 is sized to closely fit the flange 44 for compression control when the housing 10 is squeezed. The groove 48 is not so deep as to allow the plunger 14 to completely fill the cavity of manifold 46 defined within the flange 44.

The block of material 42 includes a first passage 50 conveniently extending through the block 42 from the manifold 46 to the other end of the block. This first passage 50 is incorporated in defining the valving mechanism of the flow control apparatus. Located within the first passage 50 is a valve 52. In the preferred embodiment, the valve 52 is a ball having a diameter substantially equal to the relaxed inside diameter of the first passage 50. The ball may be of dimensionally stable plastic material. The operation of the valving mechanism can be observed by reviewing FIGS. 2 and 5. In FIG. 2, the valve is closed with the ball 52 sealing the passage 50. When the housing 20 is compressed, the passage 50 is distorted to break the seal with the ball 52 and allow flow therearound. To contain the ball 52 within the operative area of the passage 50, a post 54 extends downwardly from the plunger 14. The ball is naturally incapable of rising above the distal end of this post 54. To constrain the ball 52 and yet allow flow from the passage 50, an upstanding tube 56 formed integrally with the hollow body 12 is associated with the through passageway 16 to form an outlet from the central cavity. The tube 56 includes a lip with upraised portions 58 on opposite sides thereof. The upraised portions 58 retain the ball 52 from seating into the tube 56.

A second passage 60 is provided conveniently through the resilient block 42 from the manifold 46 to the other end thereof. The second passage is located at the opposite end of the manifold cavity 46 and has a capillary 62 located therein. The capillary 62 may be selected from any conventional capillary depending on the amount of flow desired. Such capillaries are normally of glass and are rigid such that they cannot be deformed in the present application.

Located below the capillary is an upstanding tube 64 formed integrally with the hollow body 12. The tube 64 also forms part of the outlet, draining into the through passageway 16. The outer dimension of the tube 64 is substantially equal to the outer dimension of the capillary 62 to conveniently fit snugly within the second passage 60. The tube 64 also acts to prevent the capillary from sliding into the through passageway 16.

Located intermediate the first and second passages 50 and 60 is a space 66. The space 66 is positioned adjacent the first passage to allow exaggerated deformation of the wall of the passage 50 when the resilient block 42 is compressed. The space 66 extends only partially through the block 42 to avoid flow therethrough. An upstanding pin 68 also formed integrally with the hollow body 12 acts to control the deformation of the wall of the passage 50 into the space 66 as can best be seen in FIG. 5.

Looking then at the operation of the preferred embodiment, the through passageway 16 may conveniently be placed via passageway end 18 in communication with monitoring equipment or a controlled source of fluid. The opposite end of the through passageway 16 is connected to the catheter or other distribution mechanism for the monitored liquid. The inlet 34 is coupled with a source of fluid which is to slowly flow into the catheter for inhibiting clotting at the end thereof. Under normal operation, medical fluid introduced through inlet 34 passes in a low volume flow through the capillary 62 and into the through passageway 16. When flushing of the system, or additional clearing of the catheter is required, an operator may grip the housing 10 so as to squeeze the two parts, the hollow body 12 and the plunger 14, toward one another. As the housing is squeezed, the plunger, acting primarily on the upstanding flange 44 on the block 42, compresses the resilient material of the block 42 and distorts the passage 50 as illustrated in FIG. 5. This distortion allows high volume flow around the ball valve 52 and into the outlet. Release of the housing 10 removes the compression force from the resilient block 42 allowing the device to return to its relaxed state. In doing so the passage 50 closes around the valve 52 and seals the passage once again.

Thus, an improved flow control apparatus capable of being manipulated with one hand is disclosed. While embodiments and applications of this application have been shown and described, it would be apparent to those skilled in the art that many more modifications are possible without departing from the inventive concepts herein. The invention, therefore, is not to be restricted except by the spirit of the appended claims.

What is claimed is:

1. A flow control apparatus comprising
a housing having a hollow body and a plunger slidably positioned in and extending from said hollow body, said housing including a central cavity defined by said hollow body and said plunger, an inlet into said central cavity and an outlet from said central cavity;
a block of resilient material positioned in said central cavity between said inlet and said outlet and having a first passage therethrough oriented to provide communication between said inlet and said outlet and a second passage therethrough oriented to provide communication between said inlet and said outlet, said second passage including a rigid flow restrictor therein; and
a valve in said passage.

2. The apparatus of claim 1 wherein said inlet is in said plunger and said outlet is in said hollow body.

3. The apparatus of claim 1 wherein said valve is a ball having a diameter substantially equal to the inside diameter of said first passage.

4. The apparatus of claim 1 wherein said housing forms a squeezable hand grip.

5. The apparatus of claim 1 wherein said block includes a manifold adjacent a first end of each of said first and second passages and with one of said inlet and said outlet.

6. The apparatus of claim 1 wherein said outlet is a through passageway in communication with said first passage.

7. A flow control apparatus comprising
a rigid housing having two parts defining a cavity therein, said two parts being constructed and arranged to be squeezed together to reduce the size of said cavity, said housing further including an inlet into said cavity and an outlet from said cavity;
a block of resilient material positioned in said cavity between said inlet and said outlet and having a first passage therethrough oriented to provide communication between said inlet and said outlet and a second passage therethrough oriented to provide communication between said inlet and said outlet, said second passage including a rigid flow restrictor therein;
space within said cavity not filled with resilient material to allow deformation of said block; and
a valve in said first passage.

8. The apparatus of claim 7 wherein said valve is a ball having a diameter substantially equal to the inside diameter of said first passage.

9. The apparatus of claim 7 wherein said block of resilient material further includes a second passage therethrough oriented to provide communication between said inlet and said outlet, said second passage having a rigid flow restrictor positioned therein.

10. The apparatus of claim 9 wherein said block of resilient material further includes a manifold adjacent one end of each of said first and second passages.

11. The apparatus of claim 7 wherein said space is adjacent and not in communication with said first passage and said valve therein.

12. A flow control apparatus comprising
a housing having a hollow body and a plunger slidably positioned in and extending from said hollow body, said housing including a central cavity defined by said hollow body and said plunger, an inlet into said central cavity and an outlet from said central cavity;
a block of resilient material positioned in said central cavity between said inlet and said outlet and having a first passage therethrough oriented to provide communication between said inlet and said outlet and a second passage therethrough oriented to provide communication between said inlet and said outlet, said second passage including a rigid flow restrictor therein;
space within said cavity not filled with resilient material to allow deformation of said block; and
a valve in said first passage.

* * * * *